United States Patent [19]

Schwarz et al.

[11] 4,028,347

[45] June 7, 1977

[54] METHOD FOR PROCESSING LACTAM RESIDUES WHICH CONTAIN BORIC ACID

[75] Inventors: Hans-Helmut Schwarz, Krefeld-Traar; Otto Immel, Krefeld, both of Germany

[73] Assignee: Bayer Aktiengesellschaft, Germany

[22] Filed: June 5, 1975

[21] Appl. No.: 584,219

Related U.S. Application Data

[63] Continuation of Ser. No. 395,714, Sept. 10, 1973, abandoned.

[30] Foreign Application Priority Data

Sept. 15, 1972 Germany .......................... 2245300

[52] U.S. Cl. .................... 260/239.3 A; 260/293.86
[51] Int. Cl.² ........................................ C07D 201/16

[58] Field of Search ............... 260/239.3 A, 293.86

[56] References Cited

UNITED STATES PATENTS

| 3,350,393 | 10/1967 | Petri et al. ................. 260/239.3 A |
| 3,583,980 | 6/1971 | Mannsmann et al. ...... 260/239.3 A |

*Primary Examiner*—Henry R. Jiles
*Assistant Examiner*—Robert T. Bond
*Attorney, Agent, or Firm*—Connolly and Hutz

[57] ABSTRACT

Object of the invention is a process for the treatment of a lactam distillation residue which contains boric acid in which a polyhydric alcohol is added to the crude lactam. By these means the formation of deposits and incrustations on the heating surfaces of the distillation apparatus can be prevented.

6 Claims, No Drawings

METHOD FOR PROCESSING LACTAM RESIDUES WHICH CONTAIN BORIC ACID

CROSS-REFERENCE TO RELATED APPLICATION

This application is a continuation of application Ser. No. 395,714 filed Sept. 10, 1973 and now abandoned.

This invention relates to a method for processing lactam residues which contain boric acid.

The catalytic re-arrangement of oximes to lactams in the gaseous phase is mainly carried out on catalysts which contain boric acid, but boric acid is already volatile at the reaction conditions required and the reaction product consequently contains boric acid as an impurity.

Since lactams are required to be in a very high state of purity for subsequent use, purification processes are essential. These purification processes, which have been numerously described in the literature, generally include a distillation stage. Lactam which is free from boric acid can easily be obtained from lactam contaminated with boric acid by such a distillation but, to purify the resulting distillation residues so that they are substantially free from lactam is very difficult because the boric acid in the residues undergoes reactions which result in the formation of deposits and incrustations on the heating surfaces of the distillation apparatus, even if the evaporation is carried out in a heat exchanger such as a thin-layer evaporator in which the substance to be evaporated is kept in motion and allowed to stay only a short time. The quantities of lactam remaining in the distillation residues can generally no longer be isolated and must therefore be discarded.

The deposits and incrustations are caused partly by the formation of lactam polymers, which is catalysed by boric acid, and partly by the reaction of boric acid with caprolactam to form lactam-N-metaborate. This reaction between boric acid and caprolactam takes place when caprolactam which contains boric acid is heated to about 160° C, a temperature which occurs in the sump of the distillation column during the distillation process.

It has now been found that the formation of deposits and incrustations on the heating surfaces of the distillation apparatus can be prevented by adding polyhydric alcohols to the boric acid-containing lactam.

This invention therefore relates to a process for the treatment of a lactam distillation residue which contains boric acid, in which a polyhydric alcohol is added to the crude lactam which is then heated preferably to a temperature of from 80° to 170° C and distilled.

The method according to the invention prevents both boric acid and its addition products with lactam from being deposited in a solid form on the heating surfaces as well as the polymerisation of caprolactam caused by the boric acid present. It also makes it possible for the lactam distillation residues to be further distilled and thereby results in considerably increased lactam yields.

Polyhydric alcohols suitable for this purpose are alcohols which preferably contain 3 to 10 carbon atoms, more preferably 3 to 6 carbon atoms, e.g. propane-1,2-diol, glycerol, trimethylolpropane, hexane-1,3,5-triol, pentaerythritol and/or mannitol and mixtures of these alcohols. The quantity of alcohol used is 0.5 to 2 mol, based on the molar quantity of boric acid in the residue or based on 1 mol of boric acid present in the lactam which is to be distilled.

The polyhydric alcohol is preferably added to the crude lactam distillation residues although it may also be added to the crude lactam before distillation is begun.

The residue mixed with alcohol is heated preferably to a temperature of from 80° to 170° C, more preferably 120° to 160° C, for preferably 0.01 – 8 hours, more preferably 0.4 – 2 hours. Water is produced in this reaction and may be distilled off at normal pressure or under a vacuum or removed with a known carrier such as toluene, chlorobenzene or an inert gas such as nitrogen.

Subsequent removal of the lactam by distillation is advantageously carried out, as has long been customary in the art, by means of thin-layer evaporators equipped with rotating parts, in which the viscous products can easily be treated, but other evaporators may also be used.

The process may be applied to caprolactam distillation residues but may also be used for processing other lactams, e.g. those derived from ω-aminovaleric acid, ω-aminocaprylic acid, ω-aminoundecanoic acid or ω-aminolauric acid.

The following examples are given to explain the process but do not restrict the subject matter of the application.

EXAMPLE 1

When the crude product obtained from catalytic cyclohexanone-oxime re-arrangement according to German Offenlegungschriften No. 1,670,860 and 1,795,226 is processed, a distillation residue is obtained which, in addition to 5.1% of boric acid and 74% of lactam, contain higher boiling impurities and other non-volatile substances.

When a thin-layer evaporator equipped with rotary fittings and heated with oil which is at a temperature of 180° C is used for evaporating this residue, 50% of the residue introduced can be distilled off at a pressure of 1.5 mm. Hg.

If the distillation is continued, solid incrustations are formed on the wall of the thin-layer evaporator and prevent the operation of the wiper blades so that the distillation must be stopped.

If, however, the distillation is stopped when 50% of the quantity introduced has been distilled off, approximately 32% of the lactam originally present remain in the sump product of the evaporator and can no longer be isolated.

EXAMPLE 2

1 kg of the residue mentioned in Example 1 is mixed with 80 g of glycerol and 200 ml of toluene and refluxed in a water separator at 135° – 160° C for 6 hours. Toluene is then removed under vacuum. The resulting product which is now free from toluene is distilled in a thin-layer evaporator under the conditions described in Example 1. 720 g of caprolactam, i.e. 72% of the quantity originally introduced, are obtained as distillate.

EXAMPLE 3 a. 166 g of hexane-1,3,5-triol b. 166 g of trimethylolpropane are added to the residue mentioned in Example 1 under the conditions described in Example 2.

After removal of the water of reaction and of toluene, the lactam was distilled in a thin-layer evaporator as in Example 1. Based on the quantity of residue introduced, the quantities of distillate obtained were 71% in the case of *a*) and
70% in the case of *b*).

EXAMPLE 4

To a solution in toluene of the residue mentioned in Example 1, which solution had a toluene content of 40% based on the total quantity of mixture, are added 1.5 mol of trimethylolpropane, based on 1 mol of boric acid, and toluene is continuously removed in a distillation column which is operated at a pressure of 20 mm. Hg. The sump temperature is 160° C. The average time of stay of the product in the distillation column is 0.5 hours. Water formed by the reaction of trimethylolpropane distills off with the toluene.

The sump obtained from this continuous distillation of solvent and water is distilled in a thin-layer evaporator at a vacuum of 1.5 mm. Hg and a temperature of 185° C. 70% of caprolactam, based on the quantity of residue originally used, is obtained as distillate.

EXAMPLE 5

Comparison experiment - preparation of lactam metaborate.

When $B_2O_3$ lactam melts in which the proportion of lactam to $B_2O_3$ is greater than 2:1 are heated, two layers are formed at temperatures starting from 160° C. The lower layer is highly viscous and solidifies to a hard, glassy mass on cooling. Analysis shows it to have a $B_2O_3$ content of 26.25%. The X-ray diagram shows a peak which is characteristic for vitreous substances, and beside it numerous small reflexes indicating the presence of a small proportion of crystallised substance. The X-ray diagram is characterised by the following reflex positions (d (A)/Int.): 6.69/4; 5.65/8; 4.76/9; 4.05/10; 3.58/9; 3.53/7.

The substance is very readily soluble in water and methanol but insoluble in benzene, chloroform and tetrachloroethylene.

We claim:

1. In the method of recovering a lactam from a mixture comprising lactam and boric acid produced by rearrangement of an oxime to a lactam in the gaseous phase in the presence of a catalyst containing boric acid, said method comprising distilling said mixture to obtain lactam and a distillation residue of boric acid and lactam and then recovering lactam from said distillation residue by further distillation, the method of improving the yield of lactam recovered from said distillation residue which comprises introducing 0.5 to 2 mol, per mol of boric acid, of a polyhydric alcohol having 3 to 10 carbon atoms into said distillation residue and heating the resulting mixture to 80° to 170° C. In order to remove water produced by distilling and subsequently removing the lactam from the mixture by distillation to thereby obtain lactam substantially free of boric acid as distillate, said lactam being selected from the group consisting of caprolactam and the lactams of ω-aminovaleric acid, ω-aminocaprylic acid, ω-aminoundecanoic acid and ω-aminolauric acid.

2. The method of claim 1 wherein said polyhydric alcohol is directly added to said distillation residue.

3. The method of claim 1 wherein said polyhydric alcohol has from 3 to 6 carbon atoms.

4. The method of claim 1 wherein said polyhydric alcohol is selected from the group consisting of propane-1,2-diol, glycerol, trimethylolpropane, hexane-1,3,5-triol, pentaerythritol, mannitol and mixtures thereof.

5. The method of claim 1 wherein said lactam is caprolactam.

6. The method of claim 1 wherein said heating to 80° to 170° C. is carried out in the presence of a member selected from the group consisting of toluene and chlorobenzene.

* * * * *